United States Patent [19]

Schwarz et al.

[11] Patent Number: 5,659,076
[45] Date of Patent: Aug. 19, 1997

[54] PROCESS FOR THE PRODUCTION OF 2,5-DIANILINO-TEREPHTHALIC ACIDS

[75] Inventors: Franz Thomas Schwarz, Wolfern; Johann Altreiter, Neumarkt; Franz Möstl, St. Veit, all of Austria

[73] Assignee: DSM Chemie Linz GmbH, Linz, Austria

[21] Appl. No.: 519,350

[22] Filed: Aug. 25, 1995

Related U.S. Application Data

[62] Division of Ser. No. 324,709, Oct. 18, 1994, Pat. No. 5,491,255.

[30] Foreign Application Priority Data

Oct. 19, 1993 [AT] Austria ..................... 2096/93

[51] Int. Cl.$^6$ ..................... C07C 51/09
[52] U.S. Cl. ..................... 562/483
[58] Field of Search ..................... 562/483

[56] References Cited

U.S. PATENT DOCUMENTS

| | | | |
|---|---|---|---|
| 2,821,541 | 1/1958 | Struve | 260/471 |
| 3,031,501 | 4/1962 | Struve et al. | 260/518 |
| 3,388,149 | 6/1968 | Dien | 260/471 |
| 3,674,814 | 7/1972 | Aldridge et al. | 260/396 N |
| 4,124,768 | 11/1978 | Kirsch et al. | 560/19 |
| 4,435,589 | 3/1984 | Rolf et al. | 560/48 |
| 4,956,464 | 9/1990 | Bender et al. | 546/57 |
| 4,981,997 | 1/1991 | Schütze et al. | 562/421 |

FOREIGN PATENT DOCUMENTS

| | | |
|---|---|---|
| 0536083A1 | 4/1993 | European Pat. Off. |
| 1297614 | 8/1960 | Germany . |
| 1118215 | 11/1961 | Germany . |
| 3104644A1 | 8/1982 | Germany . |
| 415905 | 1/1967 | Switzerland . |
| 443525 | 2/1968 | Switzerland . |
| 891640 | 3/1962 | United Kingdom . |
| 1228727 | 4/1971 | United Kingdom . |
| WO9209558 | 6/1992 | WIPO . |

OTHER PUBLICATIONS

Liebermann, Esters of Succinylsuccinates and Their Reactions with Ammonia and Primary Amines, Annalen d. Chemie 404, 272–321 (1911).

Primary Examiner—José G. Dees
Assistant Examiner—Rosalynd A. Williams
Attorney, Agent, or Firm—Wenderoth, Lind & Ponack

[57] ABSTRACT

A process for the transesterification of dimethyl succinylsuccinate with one or more aliphatic alcohols which in each case have at least 2 C atoms, in the presence of an acidic catalyst and in the presence or absence of a diluent which is inert under the reaction conditions, with exclusion of oxygen and under pressure, at least one of the two methoxy groups being replaced by the oxy group corresponding to the alcohol used and use of the process in a process for the preparation of terephthalic acids and of quinacridones.

4 Claims, No Drawings

PROCESS FOR THE PRODUCTION OF 2,5-DIANILINO-TEREPHTHALIC ACIDS

This is a Rule 60 divisional application of Ser. No. 08/324,709, filed Oct. 18, 1994, U.S. Pat. No. 5,491,255.

Quinacridones have especially gained great importance as red or violet pigments in the dyestuffs industry.

In GB Patent 891,640 the basic reaction scheme is disclosed by which quinacridones are in general prepared:

1. Condensation of diethyl succinate to give the corresponding diethylsuccinyl succinate which
2. is reacted with an aniline to give diethyl 2,5-dianilino-3,6-dihydroterephthalate. This is
3. oxidized to the diethyl 2,5-dianilinoterephthalate which
4. is hydrolyzed to the 2,5-dianilinoterephthalic acid. This is finally
5. ring-closed to the quinacridone.

A number of processes follow the reaction scheme indicated, which are intended to furnish improvements with respect to one or more reaction stages in comparison with the process of GB Patent 891,640. In the known processes, however, solvents or reagents are used whose use appears questionable from the point of view of environmental protection.

According to GB Patent 891,640 itself, the oxidation and hydrolysis in reaction stages 3. and 4. are carried out in pyridine, picolines or their homologs, the use and disposal of which, however, are unpleasant and not environmentally protective. According to the procedures described in U.S. Pat. Nos. 2,821,541 or 3,674,814 "Dowtherm A", a mixture of biphenyl and diphenyl oxide, and according to WO 92/09558 xylene, is employed as a solvent. Such solvents, however, have toxic properties. In U.S. Pat. Nos. 3,031,501, 3,388,149, GB Patent 1,228,727 or U.S. Pat. No. 4,124,768, the oxidation according to reaction stage 3. using highly toxic nitro-benzenes is described.

In U.S. Pat. No. 4,981,997, the use of an oxygen-carrying agent such as anthraquinone-2-sulfonic acid and of a quaternary ammonium compound is described for the oxidation in reaction stage 3. such compounds, however, can only be removed with difficulty, if at all, from the reaction product.

In U.S. Pat. No. 4,435,589, a process according to the reaction scheme described starting from dimethyl succinate in methanol as a solvent is described, in which the oxidation according to stage 3 is carried out using air. The yields of the 2,5-dianilinoterephthalic acids prepared in this process, however, are only about 70%. The low yields are to be traced back according to EP-A1-0 536 083 to the low solubility of dimethyl succinate and its secondary products, which are formed according to the reaction scheme described, in a solvent. In EP-A1-0 536 083, it is therefore proposed to transesterify dimethyl succinate using aliphatic alcohols which have 2 to 6 C atoms, and to employ the transesterification products which, on account of the longer hydrophobic side chains, have a higher solubility in organic solvents, for the preparation of quinacridones according to the reaction scheme described. According to the examples, however, the reaction, which is carried out in the presence of metal alkoxide, in no case takes place completely, so that the reaction mixture always contains considerable amounts of unreacted dimethyl succinate. The solubility of the correspondingly prepared dialkyl succinate, methyl alkyl succinate and dimethyl succinate mixture does not appear to be very much improved in organic solvents compared with that of dimethyl succinate on its own, because according to the examples the toxic mixture of biphenyl and diphenyl oxide (Dowtherm A) already described also has to be used for the reaction of the transesterified succinates.

It has now unexpectedly been found that dimethyl succinylsuccinate can be transesterified using an alcohol which has at least 2 C atoms, virtually no dimethyl succinylsuccinate remaining unreacted. This was completely unexpected, because from Helvetica Chimica Acta, Col. 62, Vol. 5 (1979), pp. 1682 to 1687, it is known that dimethyl succinate cannot be transesterified, in contrast to diethyl succinate, on account of the unusual stability of the methyl ester bonds.

The succinylsuccinates transesterified according to the invention and their secondary products according to the above reaction scheme in this case have a better solubility than dimethyl succinylsuccinate and its secondary products in environmentally protective organic solvents, such as alcohols, and can therefore be employed in an environmentally protective process for the preparation of 2,5-dianilinoterephthalic acid in an alcoholic solvent, the yields being unexpectedly high. The 2,5-dianilinoterephthalic acids prepared in this manner in environmentally protective solvents according to the reaction scheme described are ring-closed to the quinacridones as usual.

The invention therefore relates to a process for the transesterification of dimethyl succinylsuccinate, which is characterized in that dimethyl succinylsuccinate is reacted with one or more aliphatic, straight-chain, branched or cyclic monoalcohols which are unsubstituted or substituted by phenyl groups end in each case have 2 to 22 C atoms, in the presence of an acidic catalyst and in the presence or absence of a diluent which is inert under the reaction conditions, with exclusion of oxygen and under pressure, at least one of the two methoxy groups being replaced by the oxy group corresponding to the alcohol used.

Dimethyl succinylsuccinate can be prepared as usual by condensation of 2 mol of dimethyl succinate, which is an easily obtainable product produced on a large scale.

Alcohol is to be understood as meaning a straight-chain, branched or cyclic aliphatic monoalcohol which has 2 to 22, preferably 2 to 16, particularly preferably 3 to 8 C atoms, for example ethanol, propanol, butanol, hexanol, octanol, dodecanol, eicosanol or their isomers such as isopropanol, isobutanol, 2-methylhexanol, cyclopentanol, cyclohexanol, cyclooctanol or a mixture of such alcohols, it being possible for the alcohol to be unsubstituted or substituted by aryl groups, preferably phenyl groups, such as, for example, benzyl alcohol. Preferably, an unsubstituted, aliphatic, straight-chain or branched alcohol having 3 to 8 C atoms is employed. Preferably, only one alcohol is employed and not a plurality of alcohols.

The acidic catalysts employed are mineral acids, for example sulfuric acid, hydrochloric acid, nitric acid, preferably sulfuric acid, strongly acidic cation exchangers or organic sulfonic acids, such as p-toluene-sulfonic acid, preferably mineral acids.

The reaction can take place directly in the desired alcohol if this is liquid under the reaction conditions, or a diluent which is inert under the reaction conditions is added. Suitable inert diluents are, for example, aliphatic hydrocarbons, such as pentane, hexane, cyclopentane or cyclohexane, ethers, such as tetrahydrofuran, or mixtures of such diluents.

To carry out the reaction according to the invention, dimethyl succinylsuccinate is mixed with the desired alcohol, the acidic catalyst and, if desired, the diluent and heated under pressure with exclusion of oxygen.

At least 2 mol of alcohol per mole of dimethyl succinylsuccinate are employed, but in general an excess of at least 5 mol of alcohol per mole of dimethyl succinylsuccinate. If the alcohol is liquid under the reaction conditions, the reaction can be carried out directly in the desired alcohol, in this case at least a four-fold molar amount of alcohol being employed relative to dimethyl succinylsuccinate.

The optimum amount of the diluent is easy to determine by simple preliminary experiments using various amounts. The acidic catalyst is employed in catalytic amounts, i.e. in amounts of about 0.1 to 10 mol percent relative to dimethyl succinylsuccinate.

The reaction mixture is heated in a pressure-tight vessel with exclusion of oxygen. For this purpose, an inert gas atmosphere is built up as usual, for example, using nitrogen, helium or argon. The reaction temperatures are from about 60° to 220° C., preferably from 80° to 210° C., particularly preferably from 90° to 160° C. The reaction is in this case carried out under the resulting pressure, regulation using the inert gas pressure being possible. The pressure is in general from about 1 to 20 bar, preferably 2 to 6 bar.

When carrying out the process according to the invention, at least one of the two methoxy groups of the dimethyl succinylsuccinate is replaced by the corresponding alkoxy group of the alcohol used, virtually no unreacted starting material remaining. In general, a mixture of dialkyl succinylsuccinate and alkyl methyl succinylsuccinate results, the alkyl moiety corresponding to the alkyl moiety of the alcohol employed for the reaction. The amount of dialkyl succinylsuccinate in the product mixture in this case is all the higher, the higher the reaction temperature and the longer the reaction time. If an alcohol mixture is used, mixtures of succinylsuccinates corresponding to the alcohols used result.

The reaction course is monitored as usual, advantageously by chromatography. Depending on the amount of dialkyl succinylsuccinate desired in the product mixture, in any case at the earliest after consumption of the dimethyl succinylsuccinate in the reaction mixture, the reaction is terminated and the reaction mixture cooled. The reaction products here are in general precipitated in crystalline form. They are isolated as usual, for example by filtration or centrifuging off. In special cases a purification, for example by recrystallizing, can be added.

The process according to the invention yields methyl alkyl succinylsuccinates and dialkyl succinylsuccates in which the alkyl groups correspond to those alcohols used for the reaction. Succinates of this type can he employed in many different types of chemical syntheses. The products, however, are especially employed for the environmentally protective synthesis of 2,5-dianilinoterephthalic acids, which are a preliminary stage in quinacridone synthesis. In this synthesis, it does not matter whether in the process according to the invention mixtures of methyl alkyl succinylsuccinates and dialkyl succinylsuccinates in general result, as the esters are hydrolyzed to the acid in the later synthesis stage 4. of the above reaction scheme, so that in any case homogeneous products result from the hydrolysis stage.

The invention therefore also relates to a process for the preparation of 2,5-dianilinoterephthalic acids of the formula

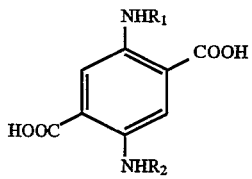

I in which $R_1$ and $R_2$ are identical or different and in each case are a phenyl or naphthyl group which is unsubstituted or mono- or polysubstituted by halogen, nitro, alkyl, alkoxy, phenyl, phenoxy or trifluoromethyl or by alkyl-substituted carbamoyl groups, at least one of the alpha positions of the C atom to which the amino group is bonded being unsubstituted, which is characterized in that a) dimethyl succinylsuccinate is heated with one or more alcohols of the formula

II in which $R_3$ is an alkyl group which is unsubstituted or substituted by phenyl and has 2 to 22 C atoms, in the presence of an acidic catalyst under pressure at temperatures from 60° to 180° C., a compound of the formula

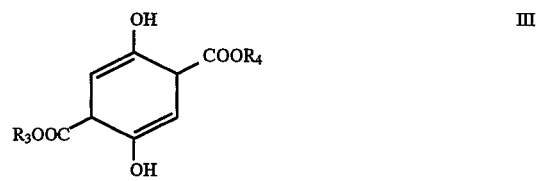

III in which $R_3$ has the abovementioned meaning and $R_4$ has the meaning of $R_3$ or is additionally a methyl group, $R_3$ and $R_4$ in the formula III being exchangeable, being obtained, b) the reaction product from stage a) is heated to temperatures of 40° to 150° C. after or without isolation, optionally with addition of a diluent which is inert under the reaction conditions, with at least a two-fold molar amount of one or more amines of the formula

IV in which $R_1$ and $R_2$ have the abovementioned meaning, in the presence of acid, a compound of the formula

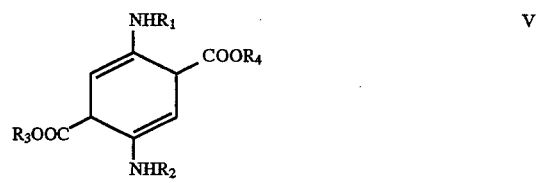

V in which $R_1$, $R_2$, $R_3$ and $R_4$ have the abovementioned meanings, being obtained, c) the reaction product from stage b) is treated with acid until the reaction is acidic and heated to temperatures of 50° to 100° C. after or without isolation, optionally with addition of a diluent which is inert under the reaction conditions, after which air is blown into the reaction mixture, the terephthalate ester of the formula

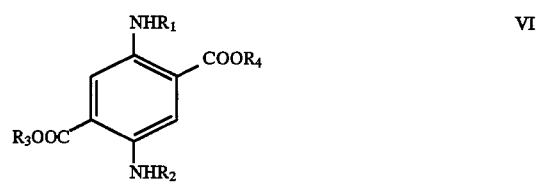

VI in which $R_1$, $R_2$, $R_3$ and $R_4$ have the abovementioned meaning, being obtained, which d) is converted with heating after or without isolation, optionally with addition of a diluent which is inert under the reaction conditions, by reaction with a compound of the formula M—OH, in which M is a metal, to a compound of the formula

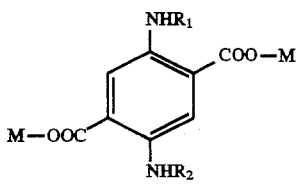

which e) is treated with water and acid until the reaction is acidic and allowed to react after or without isolation, optionally with addition of a diluent which is inert under the reaction conditions to give the terephthalic acid of the formula I which is isolated from the reaction mixture.

The process with the exception of stage a. is carried out in a manner disclosed in one of the cited literature references, but in an alcohol of the formula II as a diluent or in one of the inert diluents indicated for stage a.

The reaction stage a) is carried out according to the invention, the alcohol of the formula $R_3OH$ in which $R_3$ has the abovementioned meaning preferably being employed simultaneously as a diluent. Preferably, $R_3$ is a straight-chain or branched alkyl group having 3 to 8 C atoms. Preferably, only one alcohol is employed and not a plurality of alcohols.

Reaction stage b) is preferably carried out according to U.S. Pat. No. 4,435,589, but using a compound of the formula III as a starting material and in an alcohol of the formula II or in an inert diluent of stage a., preferably in an alcohol of the formula II as a diluent; reaction stages c) and d) are preferably carried out according to WO 92/09558, but using a compound of the formula III or of the formula V and without use of a molybdenum catalyst, without isolation of the terephthalate ester and in an alcohol of the formula II or in an inert diluent of stage a., preferably in an alcohol of the formula II as a diluent. Preferably, only one amine of the formula IV is employed, $R_1$ preferably being a phenyl group which is unsubstituted or substituted by alkyl or alkoxy groups in each case containing 1 to 4 C atoms, halogen or nitro groups, at least one of the alpha positions of the C atom to which the amino group is bonded being unsubstituted.

The reaction stage e) is preferably carried out by addition of water and of a mineral acid to the reaction mixture consisting of the terephthalate of the formula VII in an alcohol of the formula II or in an inert diluent of inert diluent of stage a., preferably in an alcohol of the formula II as a diluent.

The reaction steps a. to d. can be carried out here with or without isolation of the individual reaction products, it having been shown that in a one-pot process without isolation of individual reaction products high yields of terephthalic acid of the formula VII of about 90% relative to dimethyl succinylsuccinate are nevertheless achieved.

In a particularly preferred embodiment, dimethyl succinylsuccinate is heated to temperatures of 90° to 160° C. with an unsubstituted, aliphatic, straight-chain or branched alcohol which has 3–8 C atoms and with a mineral acid in a pressure-tight vessel in an inert gas atmosphere. After reaction is complete, the pressure in the reactor is released and the reaction mixture is heated to temperatures of 60° to 100° C. with an amine of the formula $R_1$—$NH_2$, in which $R_1$ is a phenyl group substituted by one or more alkyl groups, at least one of the alpha positions of the C atom to which the amino group is bonded being unsubstituted, after which the reaction mixture is acidified and heated to temperatures of 60° to 90° C. Air is then blown into the reaction mixture until the reaction to give the terephthalate ester of the formula VI is terminated. An alkali metal hydroxide is then added to the reaction mixture until the reaction is alkaline and the mixture is heated to reflux. After cooling, water and a mineral acid are added to the reaction mixture until the reaction is acidic. If two phases are formed here as a result of the poor miscibility with water of the diluent used, the aqueous phase is separated off, after which the terephthalic acid of the formula I in general precipitates from the reaction mixture in crystalline form and is isolated by filtration.

Also claimed is a process for the preparation of quinacridones of the formula

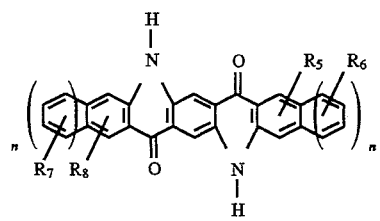

in which $R_5$, $R_6$, $R_7$ and $R_8$ are identical or different and in each case are one or more halogen atoms, nitro, alkyl, alkoxy, phenyl, phenoxy, or trifluoromethyl- or alkyl-substituted carbamoyl groups and n is the number 0 or 1, which is characterized in that terephthalic acid of the formula I is prepared according to the invention and ring-closed as usual, for example according to U.S. Pat. No. 4,956,464, to give the quinacridone of the formula VIII.

As in the process described no environmentally harmful substances have to be disposed of, the process for the preparation of dialkyl succinylsuccinates and alkyl methyl succinylsuccinate of terephthalic acids of the formula I and of quinacridones of the formula VIII represents an enrichment of the art.

EXAMPLE

A 0.5 l autoclave having a stirrer and gas inlet tube was filled with 46 g of dimethyl succinylsuccinate (0.2 mol), 250 ml of 1-butanol and 0.52 ml of concentrated sulfuric acid and closed. The reaction mixture was purged with nitrogen for 15 minutes and heated at 140° C. for 2 hours. After cooling, a precipitate was deposited which was identified by thin-layer chromatography as a mixture of dibutyl succinylsuccinate and methyl butyl succinylsuccinate. Dimethyl succinylsuccinate was only still found in traces. 26 g of p-toluidine were added to the reaction mixture, it was purged with nitrogen and heated without pressure at about 75° C. for 1 hour with further nitrogen purging. 20 ml of acetic acid were then added and the mixture was heated to reflux. After reaching the reflux temperature, air was blown into the reaction mixture for 4 hours using a dip tube. 70 g of solid potassium hydroxide were then added and the mixture was heated to reflux for a further 1 hour. After cooling, 500 ml of water were added to the reaction mixture and the pH was adjusted to 2.5 to 3 by adding sulfuric acid. After separating off the aqueous phase and again adding about 400 ml of water, a dark-violet precipitate was deposited, which was filtered off and dried at about 100° C.

In this way, 67.6 g of pure 2,3-dimethyl-dianilinoterephthalic acid, i.e. 90% of theory relative to dimethyl succinylsuccinate, were obtained. The purity was determined by means of HPLC (high pressure liquid chromatography) and was 98%.

What we claim is:

1. Process for the preparation of 2,5-dianilino-terephthalic acids of the formula

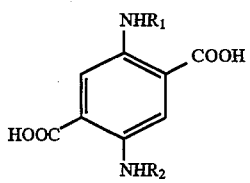

I in which $R_1$ and $R_2$ are identical or different and in each case are a phenyl or naphthyl group which is unsubstituted or mono- or polysubstituted by halogen, nitro, alkyl, alkoxy, phenyl, phenoxy or trifluoromethyl or by alkyl-substituted carbamoyl groups, at least one of the alpha positions of the C atom to which the amino group is bonded being unsubstituted, characterized in that a) dimethyl succinylsuccinate is heated with one or more alcohols of the formula

II in which $R_3$ is an alkyl group which is unsubstituted or substituted by phenyl and has 2 to 22 C atoms, in the presence of an acidic catalyst under pressure at temperatures from 60° to 180° C., a compound of the formula

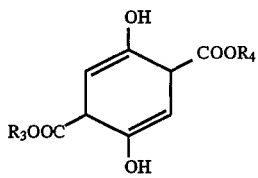

III in which $R_3$ has the abovementioned meaning and $R_4$ has the meaning of $R_3$ or is additionally a methyl group, $R_3$ and $R_4$ in the formula III being exchangeable, being obtained, b) the reaction product from stage a) is heated to temperatures of 40° to 150° C. after or without isolation, optionally with addition of a diluent which is inert under the reaction conditions, with at least a two-fold molar amount of one or more amines of the formula

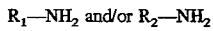

IV in which $R_1$ and $R_2$ have the abovementioned meaning, in the presence of acid, a compound of the formula

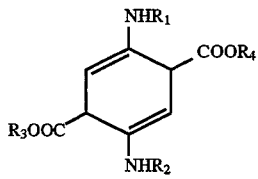

V in which $R_1$, $R_2$, $R_3$ and $R_4$ have the abovementioned meanings, being obtained, c) the reaction product from stage b) is treated with acid until the reaction is acidic and heated to temperatures of 50° to 100° C. after or without isolation, optionally with addition of a diluent which is inert under the reaction conditions, after which air is blown into the reaction mixture, the terephthalate ester of the formula

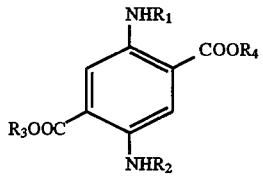

VI in which $R_1$, $R_2$, $R_3$ and $R_4$ have the abovementioned meaning, being obtained, which d) is converted with heating after or without isolation, optionally with addition of a diluent which is inert under the reaction conditions, by reaction with a compound of the formula M—OH, in which M is a metal, to a compound of the formula

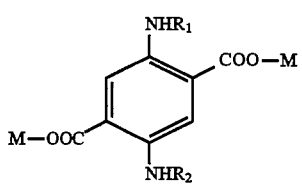

VII which e) is treated with water and acid until the reaction is acidic and allowed to react after or without isolation, optionally with addition of a diluent which is inert under the reaction conditions to give the terephthalic acid of the formula I which is isolated from the reaction mixture.

2. Process according to claim 1, characterized in that an amine of the formula IV is employed in which $R_1$ and $R_2$ are identical and are a phenyl group which is unsubstituted or substituted by halogen atoms, alkyl or alkoxy groups in each case having 1 to 4 C atoms or nitro groups.

3. Process according to claim 1, characterized in that the process is carried out in an alcohol of the formula II according to claim 1 as a diluent.

4. Process according to claim 1, characterized in that the process is carried out as a one-pot reaction.

* * * * *